United States Patent [19]

Aufdembrink et al.

[11] Patent Number: 5,036,159

[45] Date of Patent: Jul. 30, 1991

[54] CRYSTALLINE OXIDES AS CATALYSTS

[75] Inventors: Brent A. Aufdembrink, Wilmington, Del.; Arthur W. Chester, Cherry Hill; Pochen Chu, Voorhees, both of N.J.

[73] Assignee: Mobil Oil Corporation, Fairfax, Va.

[21] Appl. No.: 374,032

[22] Filed: Jun. 30, 1989

[51] Int. Cl.$^5$ .................. C07C 5/02; C07C 2/52; C07C 4/02

[52] U.S. Cl. .................... 585/275; 585/418; 585/650; 585/752

[58] Field of Search ............... 585/275, 418, 650, 752

[56] References Cited

PUBLICATIONS

H. Steinfink et al, "Identification & Structural Implications of the 90K Super Conducting Phase", Journal of American Chemical Society, 1987, 109, pp. 3348-3353.
B. Raveau et al, "Mixed-Valence Copper Oxides Related to Perovskite", American Chemical Society, 1987, Chapter 13, pp. 122-135.
L. C. Bourne et al, "Search for Isotope Effect in Superconducting Y-Ba-Cu-)", Physical Review Letters, vol. 58, No. 22, 1987, pp. 2337-2339.
E. McNamara et al, "Superconductor Metal Oxide Catalyst in a Chemiluminescence Chromatography Detector", J. of Chromatography, 452(1988).
Bednorz and Muller, "Possible High $T_c$ Superconductivity in the Ba-La-Cu-O System", Condensed Matter 64, 189-193 (1986).
Batlogg et al, "Isotope Effect in the High-$T_c$ Superconductors $Ba_2YCu_3O_7$ and $Ba_2EuCu_3O_7$", Physical Review Letters, vol. 58 (1987).

Primary Examiner—Curtis R. Davis
Attorney, Agent, or Firm—Alexander J. McKillop; Charles J. Speciale; Marina V. Schneller

[57] ABSTRACT

Ternary oxide phases, including copper oxide, which exhibit unusal electronic properties, have been determined to exhibit catalytic function for the oxidation of carbon monoxide, the hydrogenation of ethylene and the cracking of hydrocarbons.

16 Claims, No Drawings

CRYSTALLINE OXIDES AS CATALYSTS

FIELD OF THE INVENTION

Oxide phases, particularly, ternary oxide phases, containing copper which exhibit unusual electronic properties have now been demonstrated to exhibit catalytic properties in catalysis. The ternary oxide, copper containing phases, are superconductors.

SUMMARY OF THE INVENTION

Superconductivity denotes the complete absence of electrical resistance below the superconducting temperature $T_c$. It is a phenomenon occurring in some metals and alloys at very low temperatures, near the boiling points of liquid helium and hydrogen.

The invention relates to catalytic processes employing ternary oxide phases, containing copper, and exhibiting super conductivity transition temperature, $T_c$, values exceeding 19K. The oxide phases Y-Ba-Cu, La-Ba-Cu and La-Sr-Cu, exhibit unexpected properties in catalysis. Specifically, they have been shown to catalyze cracking of hydrocarbon feeds, to catalyze the hydrogenation of ethylene to ethane and to catalyze the oxidation of carbon monoxide to carbon dioxide.

DESCRIPTION OF THE INVENTION

The copper ternary oxide phases exhibiting superconductivity transition temperature of $T_c$ greater than 19 are made by providing the three oxides including copper oxides and grinding the mixture. The second oxide can be a barium, strontium or calcium oxide while a third oxide may be the oxide of a rare earth such as yttrium or lanthanum.

Although the quantities of oxides provided are not critical to realize a superconducting phase, preferably stoichiometric quantities of the oxides are admixed for grinding.

After grinding, the mixture is fired to produce the superconductor phase. Firing involves heating at temperatures of at least about 550° C. Initial heating at temperatures of at least about 550° C. can be programmed to higher temperatures in one or more stages. After firing, in incipient stages, the mixture may be reground and subsequently refired; preferably refiring is conducted at a temperature of at least 900° C. After firing, the fired mixture can be annealed in oxygen beginning at a temperature of at most 500° C. Preferably annealing is undertaken in a programmed manner down to about 200° C. in an oxygen atmosphere. Most preferably annealing is undertakem in a 100% oxygen atmosphere.

Oxidation of carbon monoxide to carbon dioxide is undertaken by contacting the carbon monoxide with stoichiometric amounts of oxygen at temperatures of at least 600° F., preferably at at least 800° F. in the presence of the catalysts.

Hydrogenation of ethylene to ethane is undertaken by passing stoichiometric quantities of ethylene and hydrogen over the catalysts at a temperature of at least 300° F. Cracking of hydrocarbons in the presence of these catalysts must be undertaken above 800° F.

THE EXAMPLES

Preparations of the superconducting oxides were carried out by grinding intimately the stoichiometric quantities of the component metal oxide salts with a mortar and pestle. Regrinding and refiring were carried out for all reaction mixtures to ensure that complete reaction products were obtained. In the case of $YBa_2Cu_3O_{6.8}$ annealing in an $O_2$ atmosphere was also carried out. All reactions were carried out on powdered solids. The superconducting nature of $YBa_2Cu_3O_{6.8}$ was confirmed by demonstration of the Meissner effect (vis. the levitation of a SmCo magnet over samples cooled with liquid $N_2$).

Reactants, reaction conditions, and products are summarized in Table 1.

TABLE 1

Synthesis Parameters of Superconducting Oxides

| Catalyst | Reactants (Mole Ratio) | Reaction Conditions | Products |
|---|---|---|---|
| $A_1$ | $Ba(NO_3)_2$ (2)<br>$Cu(OH)_2$ (3)<br>$Y(NO_3)$ $6H_2O$ (1) | 4 h, 560° C.<br>12 h, 780° C.<br>grind<br>10 h, 850° C.<br>cool, grind<br>950° C., 12 h<br>anneal 100% $O_2$,<br>400° C. 4 hr | $YBa_2Cu_3O_{6.8}$ |
| $A_2$ | $Ba(NO_3)_2$ (2)<br>$Cu(OH)_2$ (3)<br>$Y(NO_3)$ $6H_2O$ (1) | 4 h, 560° C.<br>12 h, 900° C.<br>grind<br>12 h, 900° C.<br>anneal 100% $O_2$<br>4 h, 425° C.<br>reanneal 100% $O_2$<br>6 h, 450°<br>slow cool, 1° C./min to 200° C. | |
| $A_3$ | $Ba(NO_3)_2$ (2)<br>$Cu(OH)_2$ (3) | 4 h, 560° C.<br>12 h, 900° C.<br>grind<br>12 h, 900° C.<br>grind<br>anneal, 100% $O_2$ 450° C.<br>6 h, 1° C./min cool | $YBa_2Cu_3O_{6.8}$ |
| $A_4$ | $Ba(NO_3)_2$ (2)<br>$Cu(OH)_2$ (3)<br>$Y(NO_3)$ $6H_2O$ (1) | 4 h, 560° C.<br>12 h, 900° C.<br>grind<br>12 h, 900° C.<br>anneal, 100% $O_2$, 6 h, 450° C. | |

TABLE 1-continued

| Catalyst | Reactants (Mole Ratio) | Reaction Conditions | Products |
|---|---|---|---|
| B | $La_2(CO_3)_3 \cdot 8H_2O$ (1.85) $Ba(OH)_2H_2O$ (0.15) $Cu(OH)_2$ (1) | slow cool. 1° C./min to 200° C. 4h, 630° C. 10 h, 1000° C. grind 10 h, 100° C. | $La_{1.85}Ba_{.15}CuO_4$ |

EXAMPLE 1

Above prepared samples of varying compositions were tested for their catalytic capabilities in hydrocarbon conversion reactions. The test was carried out at three temperatures: 800°, 1000° and 1200° F. Known amounts of liquid n-hexane were injected into the gas chromatographic column via syringe pump. A ten minute on-line sample was taken and analyzed. All catalysts tested had little or no activity at 800° F., but considerable activity at higher temperatures. Calcined alumina was also treated to provide a reference. The results are listed in Table 2.

EXAMPLE 2

Above prepared samples were also tested for hydrogenation activity. Equal volumes of hydrogen and ethylene were charged into a small reactor containing granules of catalysts to be tested. The temperature ranges from 200° to 400° F. About 30 to 40% of ethylene was converted to ethane at 400° F. About 30 to 40% of ethylene was converted to ethane at 400° F. over all catalysts tested except over Gamma alumina which was included as a blank. Below 300° F., the hydrogenation activity of all catalysts reduced drastically. A 50/50 weight mixture of $Y_2O_3$ and CuO was also tested for comparison; ethylene conversion therewith was 44% under otherwise similar conditions. The details are shown in Table 3.

EXAMPLE 3

The samples were also tested for carbon monoxide and hydrocarbon oxidation activity. The hydrocarbon oxidation over catalyst samples was studied by cofeeding methane, air and nitrogen at 1000° and 1200° F. with one single detectable product which appeared to be benzene. The carbon monoxide oxidation was determined by cofeeding CO and air in a ratio of 2:5 in the temperature range of 600° to 1000° F. Gas product samples, taken at 10 minutes on stream, were analyzed by mass spectroscopy and it was found that most of CO reactants were oxidized to $CO_2$ at temperatures as low as 800° F. Quartz chips have negligible activity at similar conditions. The results are listed in Table 4.

TABLE 4

| | | | | | | | | | | | | |
|---|---|---|---|---|---|---|---|---|---|---|---|---|
| | | | | | | | | | | | | |

| | Oxidation of CO | | | | | | | | | | | |
|---|---|---|---|---|---|---|---|---|---|---|---|---|
| Catalyst | $A_1$ | | | $A_2$ | | | B | | | Quartz Chip | | |
| Temperature, °F. | 600 | 800 | 1000 | 600 | 800 | 1000 | 600 | 800 | 1000 | 600 | 800 | 1000 |
| Charge, CO, GHSV | 120 | → | → | → | → | → | → | → | → | → | → | → |
| Air, GHSV | 300 | → | → | → | → | → | → | → | → | → | → | → |
| Product Distribution | | | | | | | | | | | | |
| $CO_2$ Formed, % | 78.8 | 84.7 | 95.5 | 27.9 | 93.8 | 96.5 | 55.7 | 86.7 | 87.8 | 0 | 5.0 | 15.4 |
| Hydrocarbon, % | 0.3 | 0.3 | 0.3 | 0.4 | 0.3 | 0.2 | 0.1 | 0.4 | 0.70 | 0.9 | 1.8 | 2.8 |

TABLE 2

| | N-Hexane Cracking | | | | | | | | | |
|---|---|---|---|---|---|---|---|---|---|---|
| | Catalyst $A_1$ | | Catalyst $A_2$ | | Catalyst $A_3$ | | Catalyst B | | Gamma Alumina ($Al_2O_3$) | |
| Test Condition | 1 LHSV n-Hexane Charge, 10 min On-Line sample | | | | | | | | | |
| Temp., °F. | 1000.0 | 1200.00 | 1000.0 | 1200.0 | 1000 | 1200.0 | 1000.00 | 1200.0 | 1000.0 | 1200.0 |
| n-Hexane Conv., % | 2.8 | 56.10 | 4.8 | 53.1 | N.A. | 53.1 | 2.00 | 50.3 | 4.2 | 85.2 |
| $C_1$ | 0.2 | 7.00 | 0.5 | 6.4 | | 6.2 | 0.10 | 5.0 | 0.3 | 8.8 |
| $C_2$ | 1.2 | 22.80 | 2.0 | 22.2 | | 22.5 | 0.70 | 21.1 | 1.2 | 24.1 |
| $C_3$ | 1.2 | 13.00 | 1.5 | 12.9 | | 13.0 | 0.60 | 13.1 | 1.2 | 15.5 |
| Other Crack Prod. | — | 10.00 | 0.6 | 9.5 | | 9.5 | 0.40 | 10.6 | 1.4 | 7.3 |
| Aromatics, % | 0.2 | 3.33 | 0.2 | 2.1 | | 1.9 | 0.20 | 0.5 | 0.1 | 29.5 |

TABLE 3

| | HYDROGENATION OF ETHYLENE | | | | | | | | | | | |
|---|---|---|---|---|---|---|---|---|---|---|---|---|
| Catalyst | $A_1$ | | | $A_3$ | | | $A_2$ | | | B | | |
| Feed (GHSV) | | | | | | | | | | | | |
| Ethylene | ←600→ | | | ←600→ | | | ←600→ | | | ←600→ | | |
| $H_2$ | ←600→ | | | ←600→ | | | ←600→ | | | ←600→ | | |
| Temperature, °F. | 200 | 300 | 400 | 200 | 300 | 400 | 200 | 300 | 400 | 200 | 300 | 400 |
| Time on Stream, min. | 10 | 20 | 30 | 10 | 20 | 30 | 10 | 20 | 30 | 10 | 20 | 30 |
| Ethylene Conv., % | 0 | 3.83 | 36.51 | 0 | 0 | 33.10 | 0 | 0 | 44.99 | 0 | 0 | 33.17 |
| | | | | A*/$Al_2O_3$ | | | $Y_2O_3$/CuO | | | $A_1$ $H_2$ Reduced | | |

TABLE 3-continued

| HYDROGENATION OF ETHYLENE | | | | | | | | | | | | | |
|---|---|---|---|---|---|---|---|---|---|---|---|---|
| Catalyst | Kaiser Alumina | | | (50/50) | | | (50/50) | | | at 500° F. | | |
| Feed (GHSV) | | | | | | | | | | | | |
| Ethylene | ←300→ | | | ←300→ | | | ←600→ | | | ←600→ | | |
| $H_2$ | ←300→ | | | ←300→ | | | ←600→ | | | ←600→ | | |
| Temperature, °F. | 200 | 300 | 400 | 300 | 400 | 200 | 200 | 300 | 400 | 200 | 300 | 400 |
| Time on Stream, min. | 10 | 20 | 30 | 10 | 20 | 30 | 10 | 20 | 30 | 10 | 20 | 30 |
| Ethylene Conv., % | 0 | 0 | 0 | 86.14 | 92.74 | 94.41 | 0 | 0 | 44 | 8.8 | 40.8 | 63.9 |

*Regenerated at 1000° F. for 16 hours in air

What is claimed is:

1. A process for converting a feed containing an aliphatic of at least 6 carbon atoms, comprising contacting said feed with a ternary oxide composition of copper and two metals other than copper each of said two metals other than copper being selected from the group consisting of ytrrium, barium, calcium, lanthanum, and strontium, which ternary oxide composition exhibits super conductivity temperature $T_c$ exceeding 77K, wherein said contacting is undertaken at a temperature of at least 1000° F. and recovering ethane, ethylene or admixtures thereof.

2. The process of claim 1, wherein said temperature is at least 1000° F.

3. The process of claim 1, wherein said temperature is at least about 1200° F.

4. A process for converting a feed containing an aliphatic of at least 6 carbon atoms, comprising contacting said feed with a ternary oxide composition wherein said ternary oxide is $YBa_2Cu_3O_{6.8}$ or $La_{1.85}Ba_{0.15}CuO_4$, which ternary oxide composition exhibits super conductivity temperature $T_c$ exceeding 77K, wherein said contacting is undertaken at a temperature greater than 800° F; and recovering ethane, ethylene or admixtures thereof.

5. The process of claim 3, wherein said ternary oxide is $YBa_2Cu_3O_{6.8}$ or $La_{1.85}Ba_{0.15}CuO_4$.

6. The process of claim 4, which furthr includes producing and recovering aromatic compounds.

7. The process of claim 2, which further includes producing and recovering aromatic compounds.

8. The process of claim 2, which further includes producing and recovering aromatic compounds.

9. The process of claim 1, wherein a second metal other than copper is selected from the group consisting of barium, strontium or calcium.

10. The process of claim 1, wherein one of said two metals other than copper is yttrium or lanthanum.

11. The process of claim 9, wherein a third metal is yttrium of lanthanum.

12. A process for hydrogenating a hydrocarbon feed containing an alkene of at least two carbon atoms comprising cofeeding at least substantially equal volumes of hydrogen and said hydrocarbon feed to a catalyst reaction zone, contacting said hydrocarbon feed and hydrogen, in said catalyst reaction zone with a ternary oxide composition of copper and two metals other than copper selected from the group consisting of yttrium, barium, lanthanum, and strontium which ternary oxide composition exhibits superconductivity temperature $T_c$ exceeding 77K; undertaking said contacting at a temperature of at least 300° F.; and recovering said hydrocarbon feed with redued alkene content.

13. The process of claim 12, wherein said ternary oxide composition is $YBa_2Cu_3O_{6.8}$ or $La_{1.85}Ba_{0.15}CuO_4$.

14. The process of claim 12, wherein a second metal other than copper is selected from the group consisting of barium, strontium or calcium.

15. The process of claim 12, wherein one of said two metals other than copper is yttrium or lanthanum.

16. The process of claim 15, wherein a third metal is yttrium or lanthanum.

* * * * *

UNITED STATES PATENT AND TRADEMARK OFFICE
CERTIFICATE OF CORRECTION

PATENT NO. : 5,036,159
DATED : July 30, 1991
INVENTOR(S) : Brent A. Aufdembrink et al.

It is certified that error appears in the above-identified patent and that said Letters Patent is hereby corrected as shown below:

Column 5, line 24, after "$1000^{\circ}F$", delete the period (.) and insert a comma (,).

Column 5, line 33, "$YBa_2Cu_3O_{6.8}$" should read --$YBa_2Cu_3O_{6.8}$--.

Column 5, line 41, "furthr" should read --further--.

Signed and Sealed this

Sixth Day of April, 1993

Attest:

STEPHEN G. KUNIN

Attesting Officer

Acting Commissioner of Patents and Trademarks